US00PP14428P39

(12) United States Plant Patent
Pieters

(10) Patent No.: US PP14,428 P3
(45) Date of Patent: Dec. 30, 2003

(54) CHRYSANTHEMUM PLANT NAMED 'GEDI TWO CAS'

(50) Latin Name: *Chrysanthemum morifolium*
Varietal Denomination: Gedi Two Cas

(75) Inventor: Dirk Pieters, Staden (BE)

(73) Assignee: Pieters Plant Production, BVBA, Oostnieuwkerke (BE)

( * ) Notice: Subject to any disclaimer, the term of this patent is extended or adjusted under 35 U.S.C. 154(b) by 0 days.

(21) Appl. No.: 10/137,813

(22) Filed: May 1, 2002

(65) Prior Publication Data

US 2003/0208821 P1 Nov. 6, 2003

(51) Int. Cl.[7] ..... A01H 5/00
(52) U.S. Cl. ..... Plt./286

(58) Field of Search ..... Plt./293, 292, 298, Plt./287, 286

(56) References Cited

U.S. PATENT DOCUMENTS

PP11,908 P2 6/2001 Fuess ..... Plt./286

*Primary Examiner*—Bruce R. Campell
*Assistant Examiner*—June Hwu
(74) *Attorney, Agent, or Firm*—Knobbe, Martens, Olson & Bear, LLP

(57) ABSTRACT

A new and distinct Chrysanthemum plant cultivar is disclosed, characterized by a daisy-type inflorescence, consistent flowering response to short days, blooming consistently after 49 days of short day length, free branching habit, red/purple cylindrical ray florets, a very uniform round growth habit, and a large quantity of blooms per flowering branch.

1 Drawing Sheet

Latin name of the genus and species: The present invention relates to a new and distinct cultivar of Chrysanthemum plant, botanically known as *Chrysanthemum morifolium.*

Variety denomination: The new and distinct Chrysanthemum plant is hereinafter referred to by the cultivar name 'Gedi Two Cas.'

BACKGROUND OF THE INVENTION

The new cultivar is a product of hybridization of a female parent Chrysanthemum plant variety 'Kismo Salmon' (undistributed in the United States) and a male parent Chrysanthemum plant variety 'Tartino Yellow' (undistributed in the United States). The new cultivar was discovered and selected by the inventor in October 1997.

Asexual reproduction of the new cultivar by apical tip cutting and meristem tissue culture was performed in Oxnard, Calif. and has shown that the unique features of this cultivar are stable and reproduced true to type on successive generations.

SUMMARY OF THE INVENTION

The cultivar 'Gedi Two Cas' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'Gedi Two Cas'. These characteristics in combination distinguish 'Gedi Two Cas' as a new and distinct Chrysanthemum cultivar:

1. Daisy-type inflorescence,
2. Consistent flowering response to short days, blooming consistently after 49 days of short day length,
3. Free branching habit, 4. Red/purple cylindrical ray florets,
5. Very uniform round growth habit, and
6. Large quantity of blooms per flowering branch.

Plants of the new cultivar are similar to plants of the female parent variety, 'Kismo Salmon' in most horticultural characteristics, however plants of the new cultivar have a different flower type and differently colored ray florets than plants of the female parent variety. Plants of the new cultivar also bloom naturally one week earlier than plants of the female parent variety.

Plants of the new cultivar are similar to plants of the male parent variety, 'Tartino Yellow' in most horticultural characteristics, however plants of the new cultivar have a different flower type and differently colored ray florets than plants of the male parent variety. Plants of the new cultivar also bloom naturally two weeks earlier than plants of the male parent variety.

In comparison to the commercially available variety 'Empire Sweet Dreams' (U.S. Plant Pat. No. 11,908), 'Gedi Two Cas' blooms naturally earlier and has a smaller diameter inflorescence, more ray florets per inflorescence, and more inflorescences per flowering branch.

BRIEF DESCRIPTION OF THE PHOTOGRAPH

The photograph shows a plant of 'Gedi Two Cas' grown in a six-inch container. One cutting was used in the pot.

DETAILED BOTANICAL DESCRIPTION

In the following description, color references are made to The Royal Horticultural Society Colour Chart except where general terms of ordinary dictionary significance are used. The following observations and measurements describe plants grown in Oxnard, Calif. during the month of December and January. The age of the observed plants is 96 days from a rooted cutting. The growing temperature ranged from 55° to 68° F. at night to 60° to 75° F. during the day. Measurements and numerical values represent averages of typical flowering types.

Botanical classification: *Chrysanthemum morifolium* cultivar 'Gedi Two Cas'.
Commercial classification: Garden-type Chrysanthemum.
Parentage: Hybridization of a female parent Chrysanthemum plant variety, 'Kismo Salmon' (undistributed in the United States), and a male parent Chrysanthemum plant variety 'Tartino Yellow' (undistributed in the United States).

PROPAGATION

Time to rooting: 7 to 14 days at approximately 21° C.
Root description: Fine, fibrous.

PLANT

Growth habit: Mounding herbaceous perennial.
Height: Approximately 21.8 cm.
Spread: Approximately 22.5 cm.
Growth rate: Moderate.
Branching characteristics: Free Branching.
Length of lateral branches: Approximately 21.4 cm.
Number of leaves per lateral branch: Approximately 15.

FOLIAGE

Leaf:
- *Arrangement.*—Alternate.
- *Average length.*—Approximately 5.2 cm.
- *Average width.*—Approximately 4.6 cm.
- *Shape of blade.*—Ovate.
- *Apex.*—Cuspidate.
- *Base.*—Attenuate.
- *Attachment.*—Stalked.
- *Margin.*—Palmately lobed.
- *Texture of top surface.*—Lightly pubescent.
- *Texture of bottom surface.*—Lightly pubescent.
- *Color.*—Young foliage upper side: Near 137A. Young foliage under side: Near 138B. Mature foliage upper side: Near 137A. Mature foliage under side: Near 138B. Venation upper side: Near 145B. Venation under side: Near 138C.
- *Venation type.*—Palmately net.

Petiole:
- *Average length.*—Approximately 2.5 cm.
- *Color.*—Near 137A.
- *Diameter.*—Approximately 0.3 cm.

BLOOM

Inflorescence:
- *Flowering habit.*—Induced by darkness period greater than 13.5 hours, approximately 49 days of appropriate day length required to induce and develop blooms.
- *Inflorescence form.*—Daisy.
- *Natural flowering season.*—Approximately the middle two weeks of September.
- *Number of inflorescences per lateral branch.*—Approximately 21.
- *Inflorescence diameter.*—Approximately 5.3 cm.
- *Inflorescence depth.*—Approximately 1.5 cm.
- *Inflorescence longevity on plant.*—Approximately 17 days.
- *Persistence.*—Persistent.
- *Disc diameter.*—Approximately 1.2 cm.

Ray florets:
- *Appearance.*—Matte.
- *Texture.*—Smooth.
- *Average number per flower.*—156.
- *Shape.*—Oblong.
- *Aspect.*—Cylindrical.
- *Margin.*—Entire.
- *Apex.*—Muticous.
- *Length.*—Increasing in length gradually from approximately 1 cm (inner ray florets) to 2.5 cm (outer ray florets).
- *Width.*—Increasing in width gradually from approximately 0.1 cm (inner ray florets) to 0.3 cm (outer ray florets).
- *Color.*—Upper surface at first opening: Near 185B. Upper surface at maturity: Near 51C. Upper surface at fading: Near 64A. Under surface at first opening: Near 186C. Under surface at maturity: Near 186C. Under surface at fading: Near 186D.

Disc florets:
- *Appearance.*—Shiny.
- *Texture.*—Smooth.
- *Average number per flower.*—Approximately 33.
- *Shape.*—Cylindrical.
- *Apex.*—Obtuse.
- *Average length.*—Approximately 0.4 cm.
- *Average width.*—Approximately 0.1 cm.
- *Color.*—At first opening: Near 154B. At maturity: Near 145B. At fading: Near 12A.

Peduncle:
- *Length.*—At terminal end (shortest): Approximately 1.4 cm. At lateral end (longest): Approximately 8 cm.
- *Angle to stem.*—Acute.
- *Strength.*—Moderate.
- *Color.*—Near 144A.
- *Habit.*—Upright.
- *Diameter.*—Approximately 0.2 cm.
- *Surface texture.*—Lightly pubescent.

Inflorescence bud:
- *Length.*—Approximately 0.6 cm.
- *Diameter.*—Approximately 0.8 cm.
- *Form.*—Globular.
- *Color (as ray florets first emerge).*—Near 186C.

Involucral bracts (phyllaries):
- *Appearance.*—Matte.
- *Texture.*—Lightly pubescent.
- *Number.*—Approximately 21.
- *Shape.*—Ovate.
- *Margin.*—Entire.
- *Apex.*—Subacute.
- *Length.*—Approximately 0.7 cm.
- *Width.*—Approximately 0.4 cm.
- *Color.*—Upper side: Near 143A. Under side: Near 143A.

REPRODUCTIVE ORGANS

Ray florets:
- *Number of pistils per flower.*—1.
- *Stigma shape.*—20 Branched.
- *Stigma color.*—Near 9C.
- *Style color.*—Near 3D.
- *Style length.*—Approximately 0.6 cm.
- *Stamens.*—Absent.

Disc florets:
- *Number of pistils per flower.*—1.
- *Stigma shape.*—Two-branched.

*Sigma color.*—Near 13A.
*Style length.*—Approximately 0.4 cm.
*Style color.*—Near 154C.
*Number of stamens per flower.*—5.
*Anther shape.*—Tubular.
*Anther color.*—Near 13A.
*Pollen.*—Near 13A.

OTHER CHARACTERISTICS

Seed production: Commercially, this plant is not used or observed in a stage wherein seeds would be produced. Therefore, seed production has not been observed.

Disease resistance: Neither resistance nor susceptibility to diseases and pests has been observed in this cultivar.

Heat and cold resistance: Plants with flowers are hardy to low temperatures about −2° C. Non flowering plants are hardy in the approximate range of 3° C. to −6° C., depending upon duration of cold and amount of moisture in the soil. With adequate water plants are hardy to a high temperature of 49° C.

What is claimed is:

1. A new and distinct cultivar of Chrysanthemum plant named 'Gedi Two Cas' as herein illustrated and described.

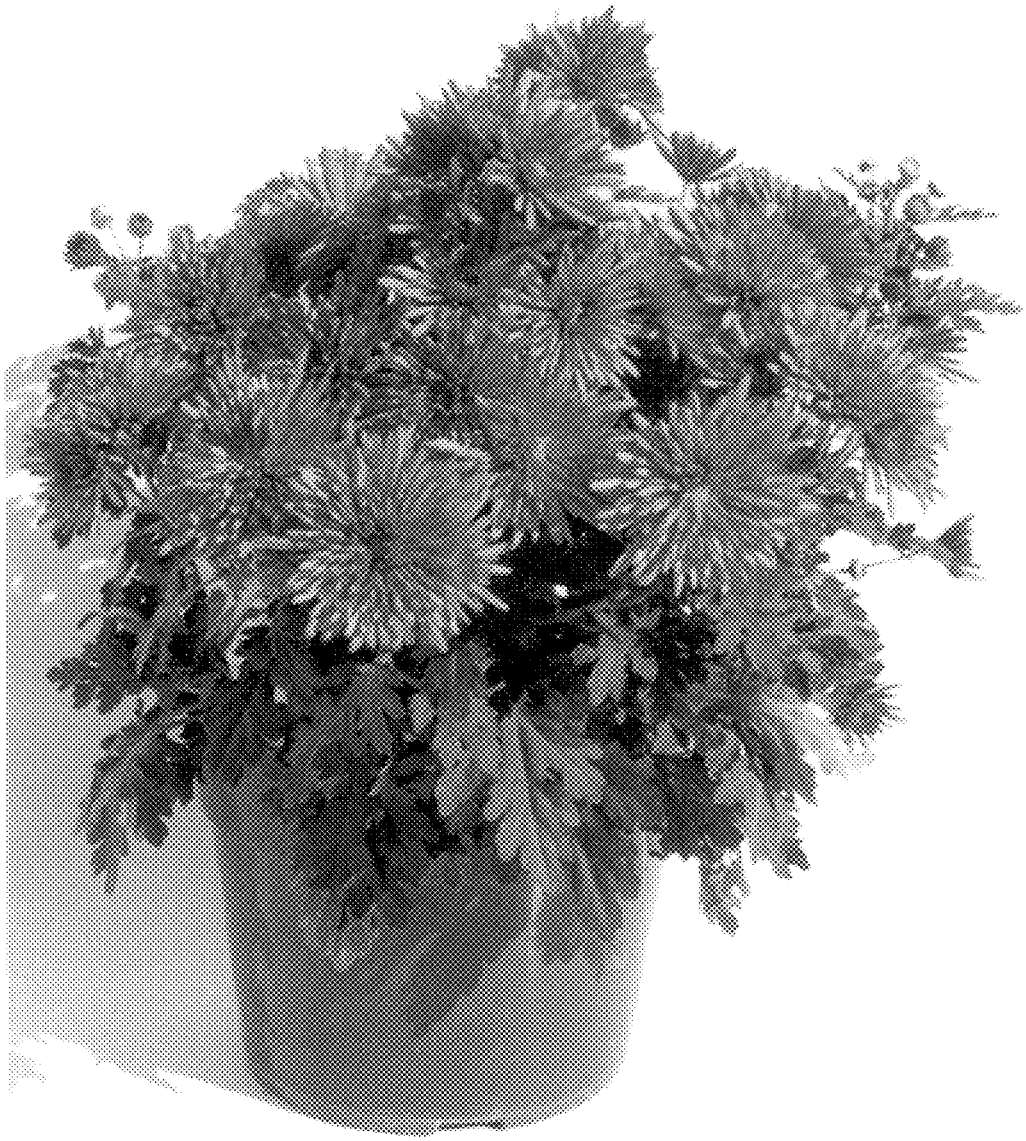

* * * * *